(12) United States Patent
Blackford

(10) Patent No.: US 8,118,726 B1
(45) Date of Patent: Feb. 21, 2012

(54) INCONTINENCY ABATEMENT SYSTEM

(76) Inventor: Richard Blackford, Venice, FL (US)

(*) Notice: Subject to any disclaimer, the term of this patent is extended or adjusted under 35 U.S.C. 154(b) by 391 days.

(21) Appl. No.: 12/387,676

(22) Filed: May 6, 2009

(51) Int. Cl.
*A61F 5/48* (2006.01)
*A63B 21/02* (2006.01)

(52) U.S. Cl. .......... 600/29; 128/845; 128/883; 128/885; 128/887; 482/105; 482/122; 482/124; 482/139

(58) Field of Classification Search .......... 128/845, 128/883–887; 600/29, 30, 37, 39, 40, 184, 600/201, 219, 235; 482/105, 122, 124, 139, 482/148
See application file for complete search history.

(56) References Cited

U.S. PATENT DOCUMENTS

| | | | |
|---|---|---|---|
| 3,916,906 A * | 11/1975 | Gerry | 606/192 |
| 4,159,153 A | 6/1979 | Yoshikawa | |
| 5,131,906 A | 7/1992 | Chen | |
| 5,356,400 A | 10/1994 | Temple | |
| 5,741,239 A | 4/1998 | Mulholland | |
| 5,865,715 A * | 2/1999 | Wallick | 482/124 |
| 6,096,057 A | 8/2000 | Klingenstein | |
| 6,206,842 B1 | 3/2001 | Tu et al. | |
| 6,258,015 B1 * | 7/2001 | Blackford et al. | 482/124 |
| 6,589,193 B2 | 7/2003 | Takashima | |
| 7,211,059 B2 | 5/2007 | Takashima | |
| 2005/0209540 A1 | 9/2005 | Takashima | |

* cited by examiner

*Primary Examiner* — Patricia Bianco
*Assistant Examiner* — Keri J Nelson

(57) ABSTRACT

A body portion fabricated of an essentially rigid material is formed of similarly configured first and second segments each shaped to include a generally spherical interior enlargement, a generally spherical exterior enlargement, an intermediate section between the enlargements, and a slit extending through the exterior enlargement and the intermediate section. The body portion pivots between a collapsed orientation with the slit at a reduced spacing and an expanded orientation with the slit at an enlarged spacing. An operational zone has a plurality of operational components. Application of a radial force to the second section by a user's external anal sphincter muscle causes axial movement of the segments to both contract and retain expanded segments and expand and retain contracted segments to reorient the system between a collapsed orientation and an expanded orientation.

3 Claims, 3 Drawing Sheets

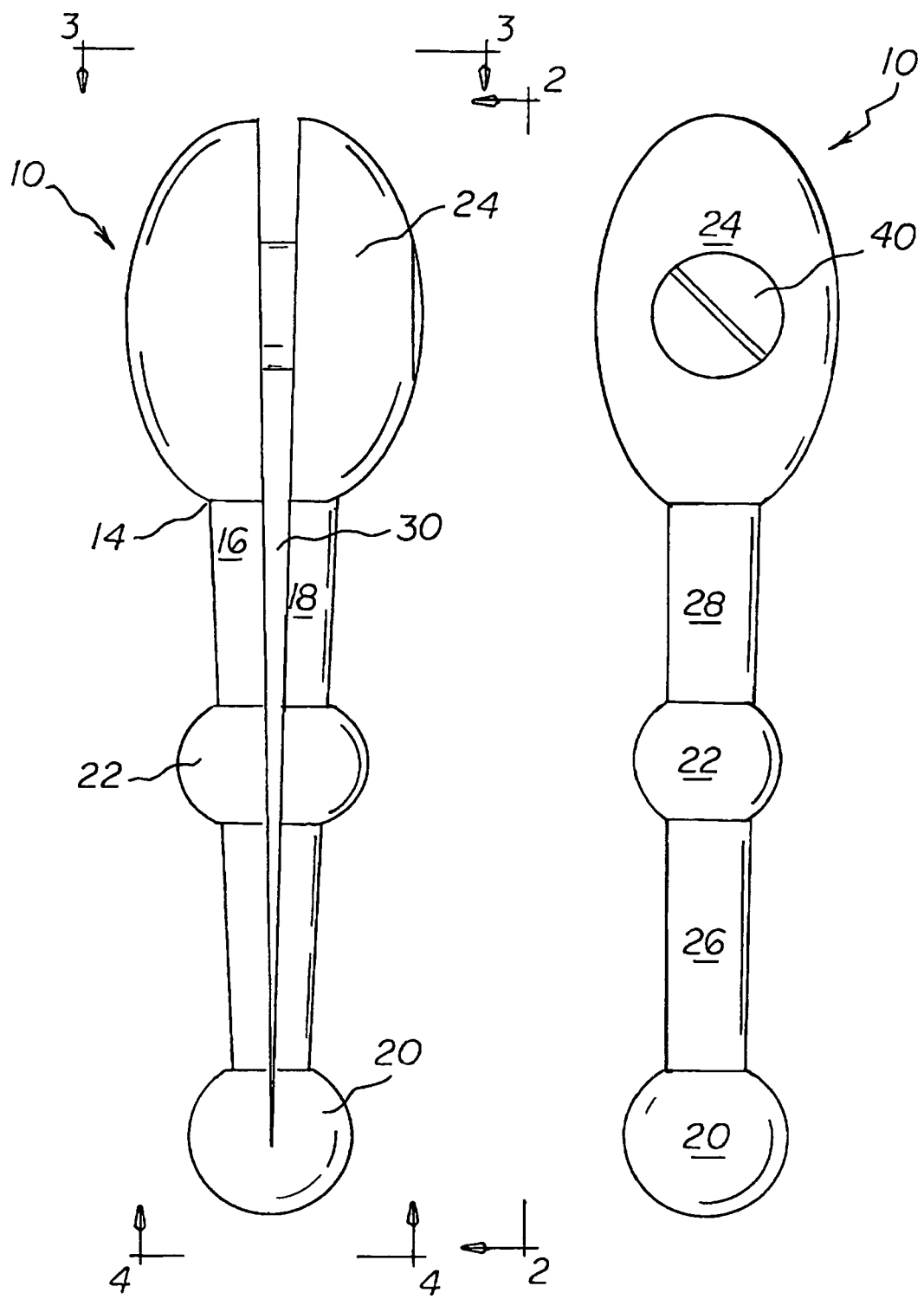

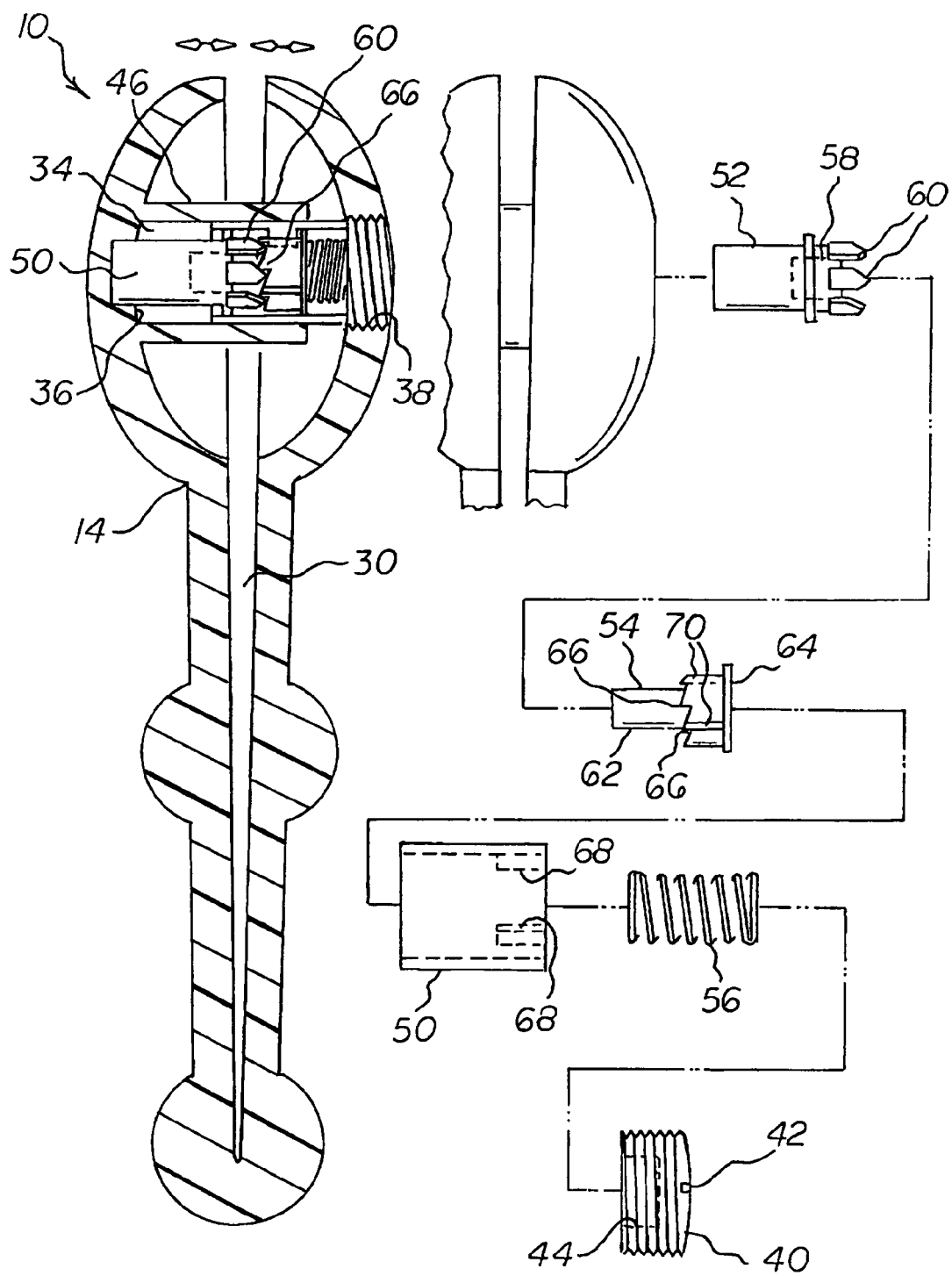

INCONTINENCY ABATEMENT SYSTEM

BACKGROUND OF THE INVENTION

1. Field of the Invention

The present invention relates to an incontinency abatement system and more particularly pertains to eliminating unintended fecal discharge in a safe, sanitary and economical manner.

2. Description of the Prior Art

The use of incontinency abatement systems of known designs and configurations is known in the prior art. More specifically, incontinency abatement systems of known designs and configurations previously devised and utilized for the purpose of eliminating unintended fecal discharge are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,159,153 to Yoshikawa issued Jun. 26, 1979 relates to a Latch Device for Drawers. U.S. Pat. No. 6,096,057 to Klingenstein issued Aug. 1, 2000 relates to a Fecal Incontinence Device and Method. U.S. Pat. No. 5,131,906 to Chen discloses an Incontinence Device. United States Published Application No. US 2005/0209540 by Takashima relates to a Hemorrhoid Massage Device. Lastly, U.S. Pat. No. 6,589,193 issued Jul. 8, 2003 to Takashima relates to a Hemorrhoid Treatment and Prostate Massage Apparatus. U.S. Pat. No. 7,211,059 issued May 1, 2007 to Takashima relates to a Hemorrhoid Treatment Device. U.S. Pat. No. 6,206,842 issued May 27, 2001 to Tu et al. relates to an Ultrasonic Operation Device. U.S. Pat. No. 5,741,239 issued Apr. 21, 1998 to Mulholland relates to an Intra-Rectal Drain and Receptacle for Fecal Incontinence. U.S. Pat. No. 5,356,400 issued Oct. 18, 1994, to Temple relates to a Large Bore Drainage Apparatus.

While these devices fulfill their respective, particular objectives and requirements, the aforementioned patents do not describe an incontinency abatement system that allows eliminating unintended fecal discharge in a safe, sanitary and economical manner.

In this respect, the incontinency abatement system according to the present invention substantially departs from the conventional concepts and designs of the prior art, and in doing so provides an apparatus primarily developed for the purpose of eliminating unintended fecal discharge in a safe, sanitary and economical manner.

Therefore, it can be appreciated that there exists a continuing need for a new and improved incontinency abatement system which can be used for eliminating unintended fecal discharge in a safe, sanitary and economical manner. In this regard, the present invention substantially fulfills this need.

SUMMARY OF THE INVENTION

In view of the foregoing disadvantages inherent in the known types of incontinency abatement systems of known designs and configurations now present in the prior art, the present invention provides an improved incontinency abatement system. As such, the general purpose of the present invention, which will be described subsequently in greater detail, is to provide a new and improved incontinency abatement system and method which has all the advantages of the prior art and none of the disadvantages.

To attain this, the present invention essentially comprises The present invention, the incontinency abatement system 10 is comprised of a plurality of components. Such components in their broadest context include a body portion and an operational zone with a plurality of operational components. Such components are individually configured and correlated with respect to each other so as to attain the desired objective.

The present invention eliminates unintended fecal discharge in a safe, sanitary and economical manner. First provided is a body portion formed of a first segment and a similarly configured second segment. The segments are shaped to include a generally spherical interior enlargement, a generally spherical intermediate enlargement, a generally spherical exterior enlargement, a frusto-conical first section 26 between the interior and intermediate enlargements, and a frusto-conical second section between the intermediate and exterior enlargements. The body portion has a V-shaped slit 30 extending through the exterior enlargement, the second section, the intermediate enlargement, the first section and a portion of the interior enlargement. A longitudinal axis extends centrally through the body portion and bisects the V-shaped slit. The body portion is fabricated of an essentially rigid plastic material for allowing the body portion to be pivoted about the interior enlargement between a collapsed orientation with the V-shaped slit at a reduced angle and an expanded orientation with the V-shaped slit at an enlarged angle.

The exterior enlargement is hollow and forms an operational zone in a cylindrical configuration with a transverse axis extending through the exterior enlargement perpendicularly through the longitudinal axis. The operational zone has an interior end with an innermost recess. The operational zone has an exterior end with a threaded aperture and a threaded cap. The cap has an exterior slot and an outermost recess facing the innermost recess. The cap is removably positioned within the threaded aperture. A cylindrical wall is integrally formed with the exterior enlargement extending from the innermost recess to a location adjacent to the cap.

Next provided is a plurality of operational components within the operational zone. The operational components include a sleeve, a first actuator, a second actuator and a coil spring. The sleeve is positioned within the cylindrical wall. The first actuator has an interior end positioned within the sleeve and within the innermost recess. The first actuator has an exterior end with an exterior recess and V-shaped teeth. The second actuator has an interior end with a projection positioned within the exterior recess of the first actuator. The second actuator has an exterior end with a shoulder. The second actuator has intermediate ramp-shaped-teeth in sliding contact with the V-shaped teeth of the first actuator. The first actuator is rotatable and the second actuator is axially shiftable. The coil spring has an interior end in bearing contact with the shoulder. The coil spring has an exterior end within the outermost recess. The sleeve has axially extending slots. The first actuator has axially extending projections slidably received within the slots to allow the axial movement of the second actuator with respect to the first actuator while the ramp-shaped teeth contact and rotate the V-shaped teeth during operation and use.

The system is adapted to be reoriented between the collapsed orientation and the expanded orientation by a user applying a radial force to the second section by the user's external anal sphincter muscle. In this manner, axial movement of the segments will both contract and retain expanded segments while axial movement of the segments will both expand and retain contracted segments.

The system is adapted to be inserted into and retained and extracted from the rectum of the user with the intermediate enlargement interior of the user's external anal sphincter muscle and the exterior enlargement exterior of the user's external anal sphincter muscle. In this manner, when in a contracted orientation the system may be inserted and extracted and when in the expanded orientation the system may be retained for the abatement of unintentional fecal discharge.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved incontinency abatement system which has all of the advantages of the prior art incontinency abatement systems of known designs and configurations and none of the disadvantages.

It is another object of the present invention to provide a new and improved incontinency abatement system which may be easily and efficiently manufactured and marketed.

It is further object of the present invention to provide a new and improved incontinency abatement system which is of durable and reliable constructions.

An even further object of the present invention is to provide a new and improved incontinency abatement system which is susceptible of a low cost of manufacture with regard to both materials and labor, and which accordingly is then susceptible of low prices of sale to the consuming public, thereby making such incontinency abatement system economically available to the buying public.

Even still another object of the present invention is to provide an incontinency abatement system for eliminating unintended fecal discharge in a safe, sanitary and economical manner.

Lastly, it is an object of the present invention to provide a new and improved A body portion fabricated of an essentially rigid material is formed of similarly configured first and second segments each shaped to include a generally spherical interior enlargement, a generally spherical exterior enlargement, an intermediate section between the enlargements, and a slit extending through the exterior enlargement and the intermediate section. The body portion pivots between a collapsed orientation with the slit at a reduced spacing and an expanded orientation with the slit at an enlarged spacing. An operational zone has a plurality of operational components. Application of a radial force to the second section by a user's external anal sphincter muscle causes axial movement of the segments to both contract and retain expanded segments and expand and retain contracted segments to reorient the system between a collapsed orientation and an expanded orientation.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a side elevational view of an incontinent abatement system constructed in accordance with the principles of the present invention.

FIG. 2 is a side elevational view of the system taken along line 2-2 of FIG. 1.

FIG. 5 is a cross sectional view taken along line 5-5 of FIG. 3.

FIG. 6 is a cross sectional view of the system of the prior Figures.

The same reference numerals refer to the same parts throughout the various Figures.

DESCRIPTION OF THE PREFERRED EMBODIMENT

Figure 3:
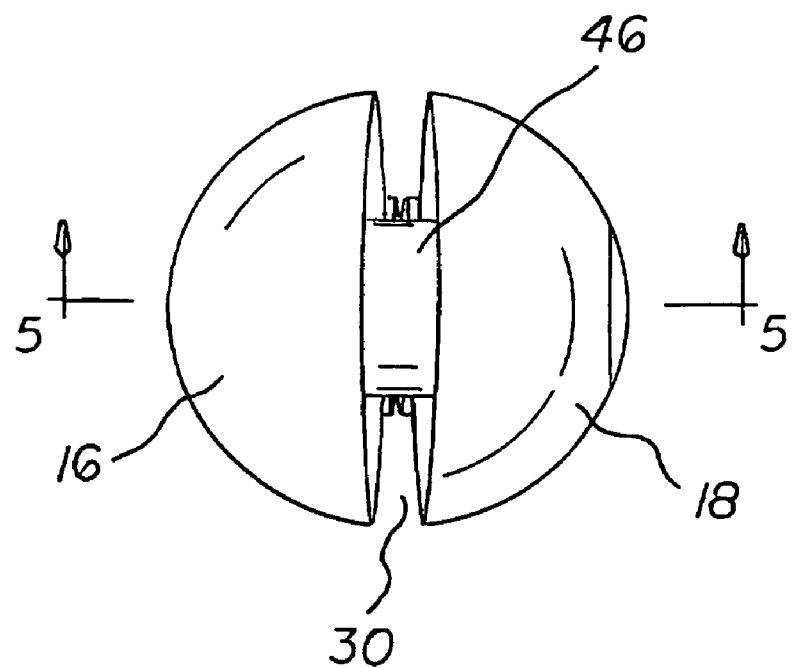
FIG. 3 is a top view of the system taken along line 3-3 of FIG. 1.
Figure 4:
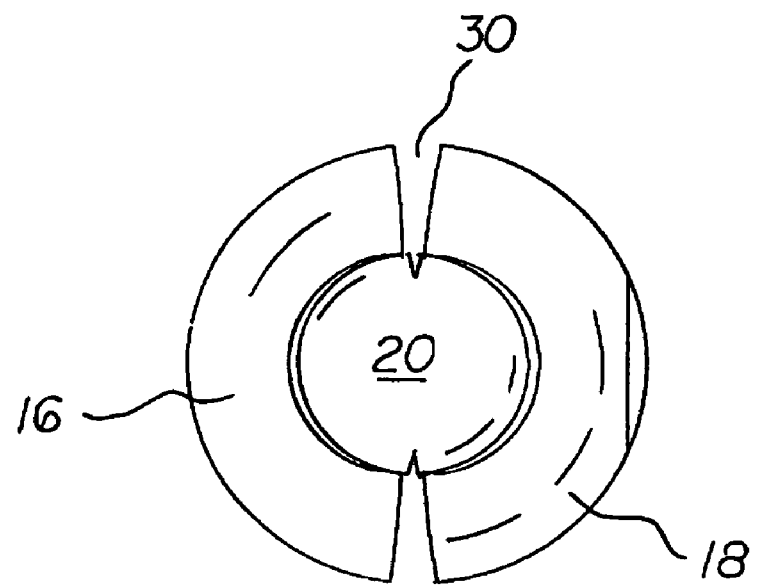
FIG. 4 is a bottom view of the system taken along line 4-4 of FIG. 1.

With reference now to the drawings, and in particular to FIG. 1 thereof, the preferred embodiment of the new and improved incontinency abatement system embodying the principles and concepts of the present invention and generally designated by the reference numeral 10 will be described.

The present invention, the incontinency abatement system 10 is comprised of a plurality of components. Such components in their broadest context include a body portion and an operational zone with a plurality of operational components. Such components are individually configured and correlated with respect to each other so as to attain the desired objective.

The present invention eliminates unintended fecal discharge in a safe, sanitary and economical manner. First provided is a body portion 14 formed of a first segment 16 and a similarly configured second segment 18. The segments are shaped to include a generally spherical interior enlargement 20, a generally spherical intermediate enlargement 22, a generally spherical exterior enlargement 24, a frusto-conical first section 26 between the interior and intermediate enlargements, and a frusto-conical second section 28 between the intermediate and exterior enlargements. The body portion has a V-shaped slit 30 extending through the exterior enlargement, the second section, the intermediate enlargement, the first section and a portion of the interior enlargement. A longitudinal axis extends centrally through the body portion and bisects the V-shaped slit. The body portion is fabricated of an essentially rigid plastic material for allowing the body portion to be pivoted about the interior enlargement between a collapsed orientation with the V-shaped slit at a reduced angle and an expanded orientation with the V-shaped slit at an enlarged angle.

The exterior enlargement is hollow and forms an operational zone 34 in a cylindrical configuration with a transverse axis extending through the exterior enlargement perpendicularly through the longitudinal axis. The operational zone has an interior end with an innermost recess 36. The operational zone has an exterior end with a threaded aperture 38 and a threaded cap 40. The cap has an exterior slot 42 and an outermost recess 44 facing the innermost recess. The cap is removably positioned within the threaded aperture. A cylindrical wall 46 is integrally formed with the exterior enlargement extending from the innermost recess to a location adjacent to the cap.

Next provided is a plurality of operational components within the operational zone. The operational components include a sleeve 50, a first actuator 52, a second actuator 54 and a coil spring 56. The sleeve is positioned within the cylindrical wall. The first actuator has an interior end positioned within the sleeve and within the innermost recess. The first actuator has an exterior end with an exterior recess 58 and V-shaped teeth 60. The second actuator has an interior end with a projection 62 positioned within the exterior recess of the first actuator. The second actuator has an exterior end with a shoulder 64. The second actuator has intermediate ramp-shaped teeth 66 in sliding contact with the V-shaped teeth of the first actuator. The first actuator is rotatable and the second actuator is axially shiftable. The coil spring has an interior end in bearing contact with the shoulder. The coil spring has an exterior end within the outermost recess. The sleeve has axially extending slots 68. The first actuator has axially extending projections 70 slidably received within the slots to allow the axial movement of the second actuator with respect to the first actuator while the ramp-shaped teeth contact and rotate the V-shaped teeth during operation and use.

The system is adapted to be reoriented between the collapsed orientation and the expanded orientation by a user applying a radial force to the second section by the user's external anal sphincter muscle. In this manner, axial movement of the segments will both contract and retain expanded segments while axial movement of the segments will both expand and retain contracted segments.

The system is adapted to be inserted into and retained and extracted from the rectum of the user with the intermediate enlargement interior of the user's external anal sphincter muscle and the exterior enlargement exterior of the user's external anal sphincter muscle. In this manner, when in a contracted orientation the system may be inserted and extracted and when in the expanded orientation the system may be retained for the abatement of unintentional fecal discharge.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An incontinency abatement system comprising:

a body portion formed of a first segment and a similarly configured second segment, the segments being shaped to include a generally spherical interior enlargement and a generally spherical exterior enlargement, an intermediate section between the enlargements, a slit extending through the exterior enlargement and the intermediate section, the body portion being fabricated of an essentially rigid material for allowing the body portion to be pivoted between a collapsed orientation with the slit at a reduced spacing and an expanded orientation with the slit at an enlarged spacing; and an operational zone with a plurality of operational components, the system adapted to be reoriented between the collapsed orientation and the expanded orientation by a user applying a radial force to the intermediate section by the user's external anal sphincter muscle whereby axial movement of the segments will both contract and retain expanded segments while axial movement of the segments will both expand and retain contracted segments, wherein the plurality of operational components include a sleeve, a first actuator, a second actuator and a coil spring, the sleeve being positioned within the exterior enlargement, the first actuator having an interior end positioned within the sleeve, the first actuator having an exterior end with an exterior recess and V-shaped teeth, the second actuator having an interior end with a projection positioned within the exterior recess of the first actuator, the second actuator having an exterior end with a shoulder, the second actuator having intermediate ramp-shaped teeth in sliding contact with the V-shaped teeth of the first actuator, the first actuator being rotatable and the second actuator being axially shiftable, the coil spring having an interior end in bearing contact with the shoulder, the coil spring having an exterior end.

2. The system as set forth in claim 1 wherein the system is adapted to be inserted into and retained and extracted from the rectum of the user with the intermediate section interior of the user's external anal sphincter muscle and the exterior enlargement exterior of the user's external anal sphincter muscle whereby when in a contracted orientation the system may be inserted and extracted while when in the expanded orientation the system may be retained for the abatement of unintentional fecal discharge.

3. An incontinency abatement system for eliminating unintended fecal discharge, the system comprising, in combination:

a body portion formed of a first segment and a similarly configured second segment, the segments being shaped to include a generally spherical interior enlargement and a generally spherical intermediate enlargement and a generally spherical exterior enlargement, a frusto-conical first section between the interior and intermediate enlargements and a frusto-conical second section between the intermediate and exterior enlargements; the body portion having a V-shaped slit extending through the exterior enlargement, the second section, the intermediate enlargement, the first section and a portion of the interior enlargement; a longitudinal axis extending centrally through the body portion and bisecting the V-shaped slit, the body portion being fabricated of an essentially rigid plastic material for allowing the body portion to be pivoted about the interior enlargement between a collapsed orientation with the V-shaped slit at a reduced angle and an expanded orientation with the V-shaped slit at an enlarged angle;

the exterior enlargement being hollow and forming an operational zone in a cylindrical configuration with a transverse axis extending through the exterior enlargement perpendicularly through the longitudinal axis, the operational zone having an interior end with an innermost recess, the operational zone having an exterior end with a threaded aperture and a threaded cap, the cap having an exterior slot and an outermost recess facing the innermost recess, the cap being removably positioned within the threaded aperture, a cylindrical wall integrally formed with the exterior enlargement extending from the innermost recess to a location adjacent to the cap;

a plurality of operational components within the operational zone including a sleeve, a first actuator, a second actuator and a coil spring, the sleeve being positioned within the cylindrical wall, the first actuator having an interior end positioned within the sleeve and within the innermost recess, the first actuator having an exterior end with an exterior recess and V-shaped teeth, the second actuator having an interior end with a projection positioned within the exterior recess of the first actuator, the second actuator having an exterior end with a shoulder, the second actuator having intermediate ramp-shaped teeth in sliding contact with the V-shaped teeth of the first actuator, the first actuator being rotatable and the second actuator being axially shiftable, the coil spring having an interior end in bearing contact with the shoulder, the coil spring having an exterior end within the outermost recess, the sleeve having axially extending slots and the first actuator having axially extending projections slidably received within the slots to allow the axial movement of the second actuator with respect to the first actuator while the ramp-shaped teeth contact and rotate the V-shaped teeth during operation and use;

the system adapted to be reoriented between the collapsed orientation and the expanded orientation by a user applying a radial force to the second section by the user's external anal sphincter muscle whereby axial movement of the segments will both contract and retain expanded segments while axial movement of the segments will both expand and retain contracted segments; and the system adapted to be inserted into and retained and extracted from the rectum of the user with the intermediate enlargement interior of the user's external anal sphincter muscle and the exterior enlargement exterior of the user's external anal sphincter muscle whereby when in a contracted orientation the system may be inserted and extracted and when in the expanded orientation the system may be retained for the abatement of unintentional fecal discharge.

* * * * *